United States Patent [19]

Nagpal

[11] Patent Number: 4,464,387
[45] Date of Patent: Aug. 7, 1984

[54] INSECTICIDAL PHENYL HYDANTOIN COMPOUNDS

[75] Inventor: Krishen L. Nagpal, Williamsville, N.Y.

[73] Assignee: Buffalo Color Corp., West Paterson, N.J.

[21] Appl. No.: 405,739

[22] Filed: Aug. 6, 1982

[51] Int. Cl.³ .................. A61K 31/415; C07D 233/74; C07D 233/72
[52] U.S. Cl. ............................... 424/273 R; 548/312; 548/314
[58] Field of Search .............................. 548/312, 314; 424/273 R

[56] References Cited

U.S. PATENT DOCUMENTS 3,668,217 6/1972 Fujinami et al. .................... 548/314
3,798,233 3/1974 Akiba et al. ......................... 548/314

OTHER PUBLICATIONS

Chemical Abstracts, 64:8028e (1966) [Konishi, K., Takeda Kenkyusho Nempo 24, 246-249 (1965)].
Chemical Abstracts, 75:110318n (1971) [Singhal, G., Ger. Offen. 2,064,474, 7/15/71].
Chemical Abstracts, 91:40311n (1979) [Eldin, S. et al., Ger. Offen. 2,829,307, 1/25/79].
Chemical Abstracts, 76:25168t (1972) [Natarajan, P., Acta Pharm. Suecica 1971, 8(5), 537-540 ].
Chemical Abstracts, 77:101615z (1972) [Singhal, G., Swiss 523,008, 7/14/72].
Chemical Abstracts, 72:90458u (1970) [Brabander, H., USP 3,494,932, 2/10/70].
Iwata, K. et al., *J. Het. Chem.*, 15, 1231 (1978).

*Chemical Abstracts,* 82:156296e [Iwata, K. et al., Japan, Kokai 74,82,662, 8/8/74].
*Chemical Abstracts,* 82:72925w (1975) [Senda, S. et al. *Tett. Lett.* 1974, (35), 3087-3088].
*Chemical Abstracts,* 84:90075q (1976) [Kakimoto, M. et al., Chem. Lett. 1976, (1), 47-48].
*Chemical Abstracts,* 84:164715x (1976) [Senda, S. et al. Hukusokan Kagaku Toronkai Koen Yoshishu, 8th 1975, 149-153].

*Primary Examiner*—Richard A. Schwartz
*Attorney, Agent, or Firm*—Michael L. Dunn; William J. Crossetta, Jr.; Arthur S. Cookfair

[57] ABSTRACT

Novel phenyl hydantoin compounds are disclosed of the structure:

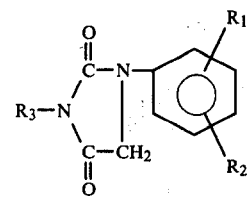

wherein $R_1$ and $R_2$ are independently hydrogen, amino, nitro, halogen, hydroxy, substituted and unsubstituted lower alkyl, cycloalkyl, phenyl and lower alkenyl; and $R_3$ is substituted and unsubstituted lower alkyl, lower alkenyl and cycloalkyl; as well as pesticidal methods employing said novel compounds; and pesticidal compositions containing said novel compounds.

5 Claims, No Drawings

INSECTICIDAL PHENYL HYDANTOIN COMPOUNDS

TECHNICAL FIELD

This invention relates to novel phenyl hydantoin compounds of the structure:

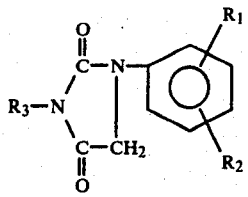

wherein $R_1$ and $R_2$ are independently hydrogen, amino, nitro, halogen, hydroxy, substituted and unsubstituted lower alkyl, cycloalkyl, phenyl and lower alkenyl; and $R_3$ is substituted and unsubstituted lower alkyl, lower alkenyl and cyclo alkyl; as well as to a method for inhibiting the growth of pests employing the novel hydantoin compounds; and to pesticidal compositions containing the novel hydantoin compounds.

BACKGROUND OF THE INVENTION

There is a continuing broad need for new products and methods which selectively eliminate, or retard the growth of undesired insects and/or nematodes hereinafter referred to as pests. Man has long recognized the special utility of various chemicals in controlling such pests. Early observations of the effect of various flowers and microorganisms on insects and nematodes resulted in their application as crude insecticidal compositions and subsequently in the synthesis of other effective insecticides and nematocides. The terms "insecticide", "nematocide", "nematocidal amount", "insecticidal amount", "pesticidal" and "pesticidal amount", as hereinafter used includes not only chemicals and amounts of chemicals which kill such pests but also that which will inhibit the growth or reproducing activity or other undesirable affect of such. The present invention addresses this broad need by providing insecticidally and nematocidally active phenyl hydantoin compounds, methods for their use, and new insecticidal and nematocidal compositions.

U.S. Pat. No. 3,846,441 discloses that various 3-phenyl hydantoins are effective herbicides, but no reference is made to the 1-phenyl hydantoins of the instant invention nor of an insecticidal or nematocidal utility therefore. Similarly, U.S. Pat. No. 3,134,663 discloses various 3-phenyl hydantoins as herbicides but there is no specific nor generic reference to the 1-phenyl hydantoins, nor of an insecticidal or nematacidal activity thereof. U.S. Pat. Nos. 3,960,883; 3,668,217 and 4,151,290 disclose various 3-phenyl hydantoins as fungicides but again, none teach the compounds of the instant invention nor their insecticidal or nematocidal utility.

DESCRIPTION OF THE INVENTION

Now, surprisingly, I have discovered novel 1-phenyl hydantoins that display effective insecticidal and nematocidal activity, these compounds being of the structure:

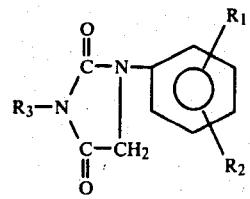

wherein $R_1$ and $R_2$ are independently hydrogen, amino, nitro, halogen, hydroxy, substituted and unsubstituted lower alkyl, cycloalkyl, phenyl and lower alkenyl; and $R_3$ is substituted and unsubstituted lower alkyl, lower alkenyl and cycloalkyl; pesticidal methods employing said novel compounds; and pesticidal compositions containing said novel compounds.

Representative lower alkyl groups assessed within the description of $R_1$, $R_2$ and $R_3$ include substituted and unsubstituted, branched and straight chain, methyl, ethyl, propyl, butyl, pentyl, hexyl and the like up to about 10 carbon atoms. Representative cycloalkyl include substituted and unsubstituted cyclobutane, cyclopentane and cyclohexane. Representative alkenyl include substituted and unsubstituted ethylene, propylene, 1-butylene, 2-butylene, 1, 2 or 3-propylene, 1,2,3 or 4 hexylene and their geometric isomers and the like up to about 10 carbon atoms. Representative substituents for the substituted alkyl, substituted alkenyl and substituted cycloalkyl include halogen, such as chlorine, bromine and fluorine, hydroxy, nitro and amino. Representative substituents for the substituted phenyl of $R_1$ and $R_2$ include lower alkyl, lower alkenyl, hydroxy, halogen, halogenated lower alkyl and alkenyl, nitro and amino.

The novel compounds of this invention are prepared by the action of aqueous or alcoholic hydrochloric acid on an appropriate substituted urea. Thus, according to the present invention compounds of the formula

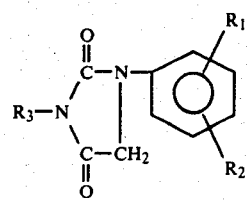

wherein $R_1$, $R_2$ and $R_3$ are as previously described, and prepared by reacting a substituted urea of the formula:

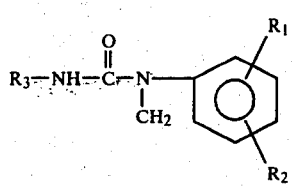

wherein $R_1$, $R_2$ and $R_3$ are as previously described with aqueous hydrochloric acid at a temperature from about 50° C. to about 120° C.

The following 1-phenyl hydantoins are illustrative of those falling within the scope of the compounds and methods of the invention: 1-phenyl-3-methyl hydantoin, 1-(p-chloro phenyl)-3-ethyl hydantoin, 1-(3-hydroxy phenyl)-3-n-butyl hydantoin, 1-(3-methyl phenyl)-3-t-butyl hydantoin, 1-(3,5-dimethyl phenyl)-3-methyl hydantoin, 1-(3,5-dichlorophenyl)-3-t-butyl hydantoin, 1-(3-chloromethylphenyl)-3-cyclohexyl hydantoin, 1-phenyl-3-butylene hydantoin, 1-phenyl-3(2-chlorohexyl) hydantoin, 1-phenyl-3-t-butyl hydantoin, 1-phenyl-3-n-butyl hydantoin, 1-phenyl-3-n-propyl hydantoin, 1-phenyl-3-ethyl hydantoin and the like.

The novel compounds of the invention may be applied directly as insecticides or nematocides of intermediates in the production thereof, or generally throughout the environment and/or medium of the insect or nematode. They may be applied as solutions, emulsions, suspensions, adducts or the like. The form of application depends upon the purpose to which it is being directed so as to insure an appropriate distribution thereof. The compounds can be formed into compositions with various conventional insect carriers, e.g. liquid or solid agents normally associated with biologically active compounds, or other active pesticidal compounds to obtain multiple or added biological effect.

Suitable carriers include clays, silicates, synthetic hydrated silicon dioxides, resins, waxes, synthetic polymeric materials, carbon, sulfur and the like. Organic materials such as walnut-shell flour, cottonseed hulls, wheat flour, wood flour or redwood-bark flour can also be used as solid carriers.

Suitable liquid carriers include water, alcohols, ketones, aromatic hydrocarbons, aliphatic hydrocarbons, chlorinated aliphatic and aromatic hydrocarbons, petroleum fractions such as kerosene and the like.

In addition to the carrier, the composition may contain a surface active agent. Such agents are those commonly known as wetting agents, disbursing agents and emulsifying agents and may be anionic, cationic or non-ionic. Examples of suitable surface-active agents include alkyl aryl sulfonates, alkyl sulfates containing more than ten carbon atoms, alkyl phenol/ethylene oxide condensates, sorbitan esters of fatty acids, alkylamide sulfonates, ethyl oxide/fatty acid ester condensates and the like. The biologically active composition may also contain other biologically active compounds, adjuvants, stabilizers, conditioners, fillers and the like.

The biologically active composition containing an inert carrier, surface active agent or other adjuvant, stabilizer, conditioner, filler or the like may be formulated as a wettable powder, a dust, granule, concentrate, solution, emulsifiable concentrate or the like.

The amount of the biologically active compound necessary to kill or inhibit the growth of various insects or nematodes will vary with the specific compound utilized, the species it is applied to, the type of formulation and the environmental condition and the like at the time of application and during the period of activity.

Under a particular set of conditions for a particular compound, in a particular formulation, the appropriate amount of compound may be readily ascertained.

The biologically active composition may contain from about 0.001 to about 98 percent by weight of the compound based upon the total weight of the composition.

Though the compounds of the instant invention display a broad range of insecticidal biological activity, various specific compounds display higher activity to various specific insects and/or nematodes. Generally the compounds of the instant invention have been found very effective on insects such as mexican bean beetle, southern army worm, bean aphid, spotted mite, spider mite and the like; and nematodes such as the root nematode and the like. It should be understood that though each of the compounds of the instant invention have at least some biological activity, the type and extent of economically desirable activity varies from compound to compound in the selection of moieties represented by various R groups. In many instances even slight changes in the R groups may result in significant changes in the activity of a compound and the pest against which it is economically effective.

The following examples are meant to illustrate the invention. Unless otherwise indicated all percentages are by weight and all temperatures in celsius.

EXAMPLE I 1-phenyl-3-isopropyl hydantoin

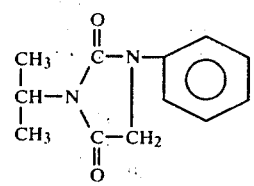

A mixture of N-phenyl glycine (0.1 mole), isopropyl isocyanate (0.12 mole) and toluene (30 ml.) was refluxed for 5 hours and then cooled. The crude product was collected by filtration and crystallized from ethanol to yield 59% of theory of the above described product having a melting point of 129° C.

In a similar manner, N-phenyl glycine (0.1 mole), n-propyl isocyanate (0.12 mole) and toluene (30 ml) was refluxed for about 5½ hours producing 13 grams (59% yield) of 1-phenyl-3-n-propyl hydantoin having a melting point of about 97° C. and the structure:

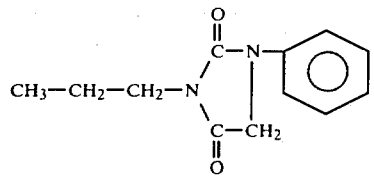

EXAMPLE II 1-phenyl-3-t-butyl hydantoin

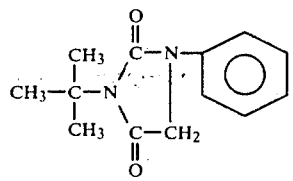

A mixture of N-phenyl glycine (0.1 mole), t-butyl isocyanate (0.12 mole) and toluene (30 ml) was refluxed for 5 hours and then cooled. The product was collected by filtration and crystallized from ethanol to produce 0.06 mole of the aforedescribed product having a melting point of 116° C.

EXAMPLE III 1-phenyl-3-n-butyl hydantoin

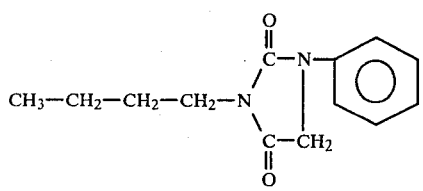

N-phenyl glycine (0.15 mole) was added with stirring over a 15 minute period to n-butyl isocyanate (0.15 mole). After the addition was complete the reaction mixture was refluxed for about 6 hours and then allowed to stand at room temperature until it solidified. The solidified mass was crystallized from ethanol and produced 0.065 moles of the above-described product having a melting point of 74° 1 C.

EXAMPLE IV 1-phenyl-3-cyclohexyl hydantoin

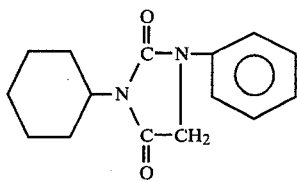

A mixture of N-phenyl glycine (0.1 mole), cyclohexyl isocyanate (0.12 mole) and toluene (30 ml) was refluxed for about 6 hours and then cooled. The crude product was recrystallized from ethanol to produce a 60% yield of the above-identified product having a melting point of approximately 196° C.

EXAMPLE V 1-phenyl-3-methyl hydantoin

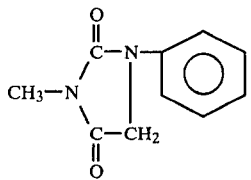

(94)

A mixture of n-phenyl glycine (22.3 grams, 0.15 moles), methylisocyanate (14.2 grams, 0.25 moles) and 30 ml of toluene was stirred at 40°-45° C. for 7 hours and allowed to stand overnight at room temperature (21° C.). The product was collected and washed with toluene, crystallized from toluene and yielded 10.5 grams (35% yield) of the above-identified product having a melting point of about 168°-170° C.

EXAMPLE VI 1-phenyl-3-ethyl hydantoin

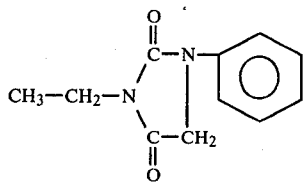

A mixture of N-phenyl glycine (30.2 grams, 0.2 moles), ethylisocyanate (17.8 grams, 0.25 moles) and 30 ml of toluene was refluxed for 9 hours and allowed to stand overnight at room temperature (21° C.). The suspended product was collected by filtration and washed with toluene. After drying (21° C.) it was crystallized from ethanol to produce 17 grams (42% yield) of the above-identified product having a melting point of about 142° C.

EXAMPLE VII

Utility

Various of the compounds of the invention presented in the examples were subjected to pesticidal tests to determine relative levels of insecticidal or pesticidal activity. The compounds were applied directly to the insect in the form of a solution. The activity of the compounds was assessed visually and rated on an activity scale of 0-10 (0=No effect; 10=very strong insecticidal or pesticidal effect). The compounds were tested for their effect on various of mexican bean beetles and rootknot nematode, with results as indicated in Table I.

TABLE I

| Compound | Pest | Lead of Activity |
| --- | --- | --- |
| 1-phenyl-3-isopropyl hydantoin | rootknot nematode | 9 |
| 1-phenyl-3-n-propyl hydantoin | rootknot nematode | 3 |
| 1-phenyl-3-t-butyl hydantoin | mexican bean beetle | 8 |
| 1-phenyl-3-n-butyl hydantoin | mexican bean beetle | 7 |
| 1-phenyl-3-methyl hydantoin | rootknot nematode | 3 |
| 1-phenyl-3-ethyl hydantoin | rootknot nematode | 3 |

I claim:
1. 1-phenyl-3-cyclohexyl hydantoin.
2. A compound selected from the group consisting of 1-(p-chlorophenyl)-3-ethyl hydantoin, 1-(3-methylphenyl)-3-t-butyl hydantoin and 1-(3,5-dichlorophenyl)-3-t-butyl hydantoin.
3. A method of killing a pest selected from the group consisting of insects and nematodes comprising contacting said pest with a pesticidal amount of 1-phenyl-3-cyclohexyl hydantoin.
4. A method of killing nematodes comprising applying to said nematodes a nematicidal amount of 1-phenyl-3-isopropyl hydantoin.
5. The method of claim 4 wherein said nematode is a rootknot nematode.

* * * * *